United States Patent
Kramer et al.

(10) Patent No.: US 6,961,616 B2
(45) Date of Patent: Nov. 1, 2005

(54) TRENDING OF CONDUCTION TIME FOR OPTIMIZATION OF CARDIAC RESYNCHRONIZATION THERAPY IN CARDIAC RHYTHM MANAGEMENT SYSTEM

(75) Inventors: Andrew P. Kramer, Stillwater, MN (US); Jeffrey Stahmann, Ramsey, MN (US); Veerichetty A. Kadhiresan, Temecula, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 344 days.

(21) Appl. No.: 09/964,972

(22) Filed: Sep. 27, 2001

(65) Prior Publication Data

US 2003/0060851 A1 Mar. 27, 2003

(51) Int. Cl.$^7$ .............................................. A61N 1/365
(52) U.S. Cl. .............................. 607/25; 607/27; 607/19
(58) Field of Search ...................................... 607/17–28

(56) References Cited

U.S. PATENT DOCUMENTS

| | | | |
|---|---|---|---|
| 5,609,613 A | | 3/1997 | Woodson et al. |
| 5,891,176 A | * | 4/1999 | Bornzin ....................... 607/18 |
| 6,144,880 A | | 11/2000 | Ding et al. |
| 6,792,310 B1 | * | 9/2004 | Turcott et al. ................ 607/27 |

* cited by examiner

Primary Examiner—George R. Evanisko
(74) Attorney, Agent, or Firm—Nikolai & Mersereau PA; C. G. Mersereau

(57) ABSTRACT

A method of optimizing cardiac resynchronization therapy delay over a patient's full range of activity for use in operating an implantable cardiac pacing device and such a device are disclosed. The method includes measuring selected conduction time between selected sites in the heart for a plurality of beats and logging the values on a periodic repeating programmable basis to produce cumulative data and constructing a current template of conduction time in relation to one or more other sensed parameters of interest over a desired range of patient activity levels. The current template is used to derive suggested optimum pacing timing.

24 Claims, 8 Drawing Sheets

TRENDING OF CONDUCTION TIME FOR OPTIMIZATION OF CARDIAC RESYNCHRONIZATION THERAPY IN CARDIAC RHYTHM MANAGEMENT SYSTEM

BACKGROUND OF THE INVENTION

I. Field of the Invention

The present invention relates generally to the operation of cardiac rhythm management systems and, more particularly, to the optimization of cardiac resynchronization therapy based on templates produced pursuant to data exhibiting trending of selected conduction times within the heart.

II. Related Art

Early cardiac pacemakers were used primarily to pace the heart when a normal conduction path from the sino-atrial (SA) node of the heart to the atrial-ventricular (AV) node or from the AV node to the ventricles was interrupted. In accordance with these events, the pacemaker was called upon to deliver ventricular stimulating pulses to maintain a pre-determined heart rate. More recently, pacemaker technology has become greatly advanced and sophisticated. For example, rate adaptive pacing has been used to vary the pre-determined rate in accordance with parameters indicative of patient activity level. In addition, techniques now involve the pacing of multiple chambers and even sequentially pacing multiple sites in the same chamber.

Thus, it is well recognized that patients having cardiac disorders may receive benefits from cardiac pacing. One such well recognized disorder is congestive heart failure (CHF). Generally, CHF refers to a cardiovascular condition in which abnormal circulatory congestion exists as a result of an inability of a heart to maintain the necessary circulatory flow rate. Circulatory congestion is a state in which the heart enlarges to compensate but the stroke volume decreases. Reduced cardiac output can be due to several disorders, including mitral regurgitation which involves a backflow or leakage of blood from the left ventricle to the left atrium and intrinsic ventricular conduction disorder which involves an asynchronous contraction of the ventricular muscle cells. These are the two common abnormalities among CHF patients and normally occur together to a greater or lesser degree in such conditions.

One recognized and accepted indication of hemodynamic performance is reflected in the patient's pulse pressure (PP) which is defined as the difference between the systolic aortic pressure and the diastolic aortic pressure. While PP can be directly used to optimize the pacing parameters in applying CHF therapy, this would require the use of a suitably positioned pressure sensor. This technique is preferably avoided because implementation of such systems require complicated measurement and none have been adapted to provide automatic optimization of cardiac performance parameters based on the measurements.

It has further been recognized that the timing of pacing may be used to provide improvements in aortic pulse pressure and that this may be achieved by adjusting the atrio-ventricular (AV) delay time or interval, which is the time interval after a sensed P-wave, to delivery of a ventricular pacing pulse to achieve a desired cardiac parameter optimization. As shown in the graphical representation of AV delay in FIG. 3, the optimization of AV delay has a profound effect on observed pulse pressure. This may be crucial to maximize the benefit of pacing, particularly for CHF patients or those with bradycardia indication. As can be seen from that figure, a longer AV delay (above 225 ms) provides little or no hemodynamic benefit; whereas an optimized AV delay of about 75 ms, for instance, can increase or boost pulse pressure by as much as 25%.

It has also been shown that optimum AV delay can be predicted from the intrinsic atrio-ventricular conduction time (AVCT) using a mathematical relationship. Such a mathematical relationship is shown and described in U.S. Pat. No. 6,144,880 to Jiang Ding et al and assigned to the same assignee as the present invention. That patent is deemed incorporated herein by reference for any purpose. It is recognized that intrinsic or natural AVCT may be a time measured between the atrial depolarization time (onset of P-wave) and any selected morphological marker of ventricular depolarization such as Q or R or S. This is further illustrated in FIG. 4 in which PQ' and PR spans are indicated.

In view of the above, a great advantage could be gained by providing a more accurate approach to the on-going determination of conduction time between two points within the heart such as AVCT and others. This could beneficially provide a more accurate and continuously updated basis for optimizing delays between sites including the AV delay whether its use suggests to the user a fixed delay value or a dynamic value which changes as a function of cardiac cycle length, activity or minute ventilation levels, or other selected parameter of interest.

SUMMARY OF THE INVENTION

The present invention provides a unique comprehensive approach to the optimization of resynchronization therapy in cardiac pacing for an individual, based on optimizing the pacing delay between two or more sites within the heart, such as atrio-ventricular (AV), ventricular-ventricular (V-V), right ventricular-left ventricular (RV-LV), right atrial-left atrial (RA-LA), etc. This is accomplished by trending a stream of data measuring a conduction time parameter of interest between the selected two points within the heart in relation to one or more sensed factors or parameters of interest such as cycle length (R-R), activity level and minute ventilation (MV), etc. Data is sensed and stored until a sufficient amount of conduction time data is collected along with other sensor data to construct a conduction time versus parameter-of-interest template which, in turn, provides a basis for optimizing the pacing delay between the corresponding pacing sites by using a developed empirical mathematical functional relationship.

This concept can be extended to include timing relationships between any two points within the heart. For example, the intrinsic delay between the LV and the RV can be used to set the interventricular delay. The actual relationship between LV-RV delay and paced LV-RV delay is not known, but an empirical relationship can be developed using template generation trending.

In other embodiments, multiple lead systems can provide data for even more sophisticated arrangements in which the optimization of resynchronization therapy involves data gathered from a plurality of pairs of points within the heart which are measured simultaneously and trended with respect to heart rate (HR), cycle length (R-R), activity level or minute ventilation (MV).

Each time conduction time is measured, it is done over a discreet programmed number of beats during an open or intrinsic (unpaced) interval. The values are averaged (preferably using exponential averaging) and the resulting averaged value assigned to the appropriate bin. In this manner, over time, data is accumulated over the range of operation of the patient's heart. If there is a sufficient number of beats averaged over a sufficient portion of the range so that a valid interpolation or extrapolation can be used, a template or other empirical relation may be developed using a best fit (linear, quadratic or higher order polynomial curve or other available known relationships, including the use of a look-up table) between the conduction time and a chosen variable of interest, generally selected from R-R or activity or MV levels. Even after a relation or template is generated, data continues to accrue so that the template may be periodically or continuously updated with new or combined data.

Using the mathematical relationship, based on the then current data, a delay selected from dynamic or fixed delays is suggested. The suggested delay can automatically be programmed into the pacer control operation and the delay function can also be changed automatically when the template is updated with new data. A dynamic delay will change automatically to compensate changes in a desired sensed variable parameter of interest such as heart rate according to the template relation.

One detailed exemplary embodiment involves the selection of data relative to the atrio-ventricular conduction time (AVCT) generating a template of AVCT versus a parameter of interest, generally R-R, activity or MV level. This detailed embodiment is intended to be an exemplary of the broader concept and is not intended to limit the claimed subject matter, the range of the invention being broader than this embodiment and others explained in the text. Yet additional embodiments will occur to those skilled in the art upon familiarization with the specification and the attached claims and their equivalents.

DETAILED DESCRIPTION

The following embodiments are described in sufficient detail to enable those skilled in the art to practice and use the invention, but it is to be understood that other embodiments may be utilized and that logical and structural changes may be made without departing from the spirit and scope of the present invention. The following detailed description is, therefore, not to be taken in a limiting sense with respect to the underlying invention.

Some of the embodiments illustrated herein are demonstrated in an implantable cardiac pacemaker which may include numerous pacing modes known in the art. However, these embodiments are illustrative of some of the applications of the present system and are not intended in an exhaustive or exclusive sense, the present system being suitable for implementation in a variety of implantable and external devices.

The present system provides a means for optimizing cardiac systolic function based on implementing the pacing delay in response to a data template or other mathematical relation generated from accumulated data relative to one or more conduction times in relation to one or more cardiac variable parameters of interest. Although cycle length, activity and minute ventilation are specifically mentioned as cardiac variable parameters of interest in this description, they are by no means limiting as to the invention and it is contemplated that others may command attention and can be employed as well.

Figure 1:
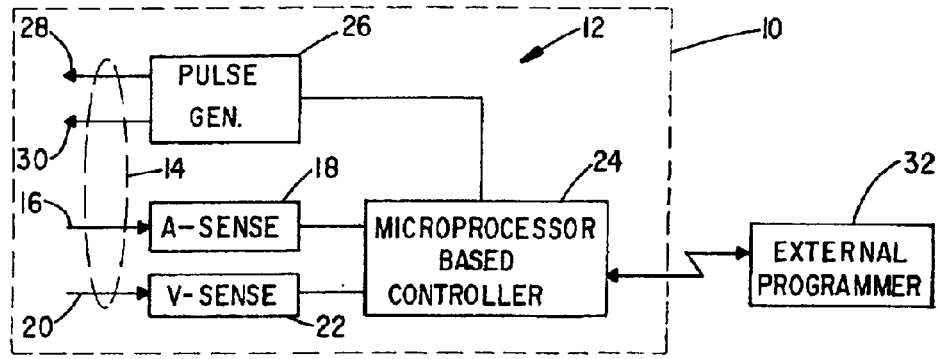
FIG. 1 is a schematic block diagram of a dual chamber cardiac rhythm management device incorporating a microprocessor-based control system for pacing in accordance with the invention.

FIG. 1 represents an embodiment of one possible implantable device capable of implementing the present invention. The figure shows a schematic representation of a cardiac rhythm management device enclosed by a dashed line box 10. The device is depicted as a VDD bradycardia pacemaker 12 which is adapted to be operatively coupled to a patient's heart by means of a conventional pacing leads 14. In particular, an atrial sensing electrode disposed in the right atrium of the heart is coupled by a wire 16 in the lead 14 to an atrial sense amplifier 18. Similarly, a ventricular sensing electrode disposed in the right ventricle is connected by a wire 20 in the lead 14 to a ventricular sense amplifier 22 contained within the pacemaker 12.

Figure 2:
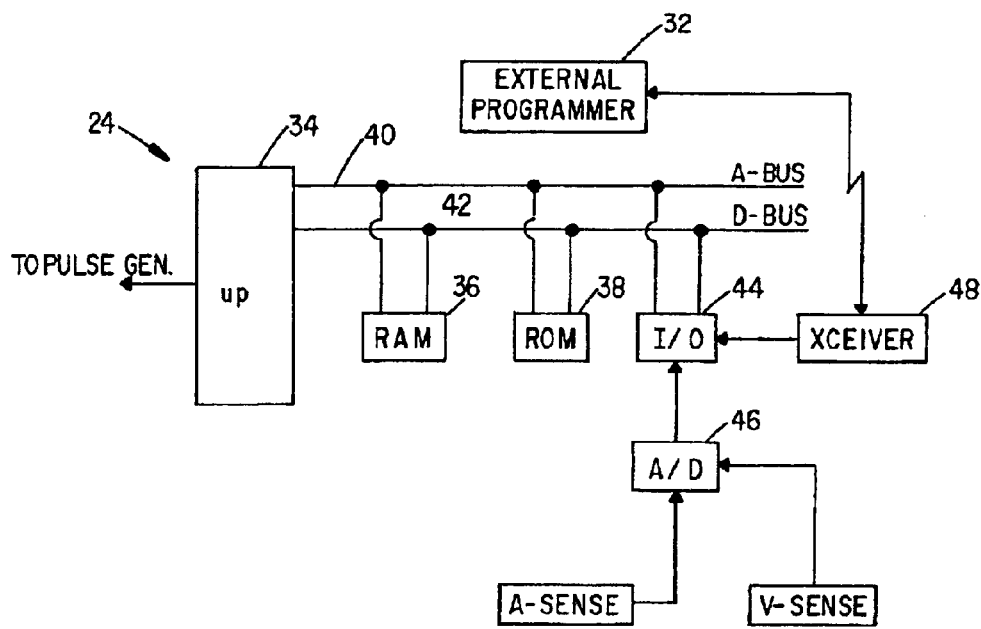
FIG. 2 is a schematic block diagram of a possible microprocessor-based controller compatible with the pacemaker of FIG. 1.
Figure 3:
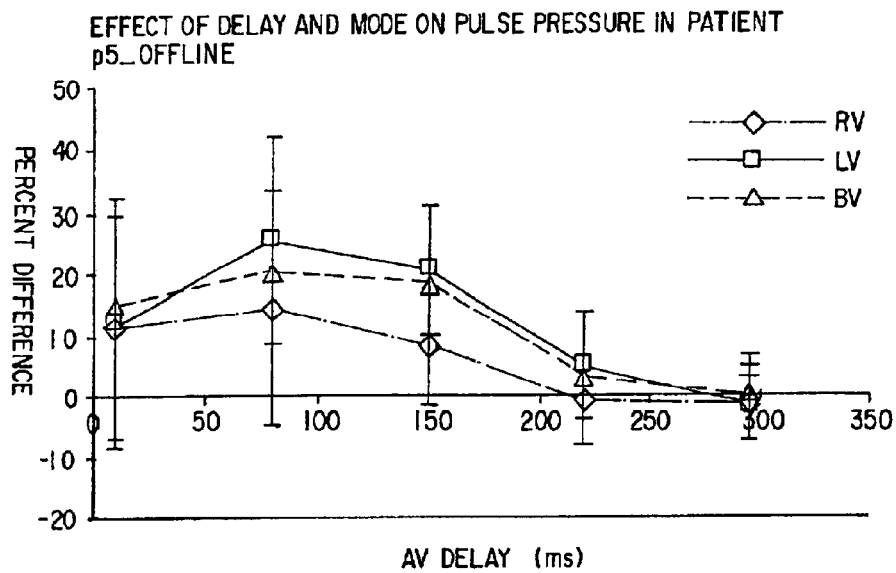
FIG. 3 is a graphical representation showing the effect of AV delay and mode on pulse pressure as a percentage deviation.
Figure 4:
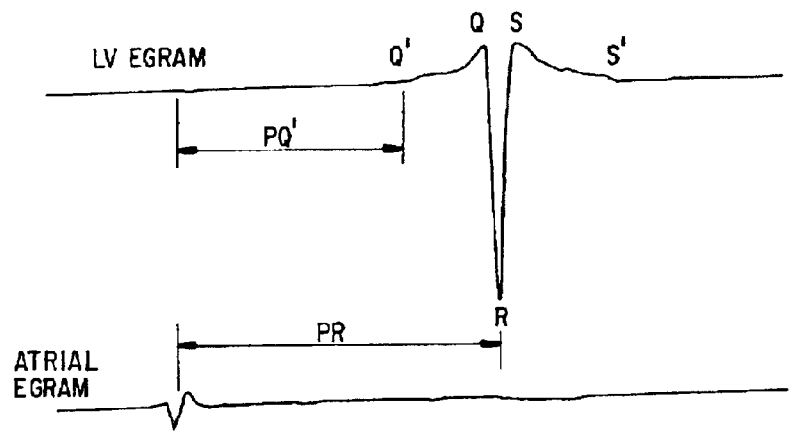
FIG. 4 is an E-gram of the left ventricle and related P-wave illustrating possible AVCT measurements (at PQ' and PR)

Thus, when the sino-atrial (SA) node in the right atrium depolarizes, the resulting signal is picked up by the atrial sense amplifier 18 and applied to a microprocessor-based controller 24 which will be more particularly described with the aid of FIG. 2. Ventricular depolarization signals (QRS-waves) are likewise amplified by the ventricular sense amplifier 22 and applied as an input to the microprocessor-based controller 24. In the same manner, other sensors (not shown) can be utilized to gather and transmit other pertinent data to the microprocessor-based in the system in a well known manner. These may include, without limitation, pressure sensors, accelerometers or other devices.

Microprocessor-based controller 24 is connected in controlling relationship to a pulse generator 26 to cause a ventricular stimulating pulse to be applied, via conductor 28 in lead 14, to tissue located proximate the apex of the right ventricle (RV) to initiate ventricular depolarization that spreads as a wave across both the right and left ventricles. The pulse generator 26 under control of the microprocessor-based controller 24 can also be made to apply stimulating pulses over a wire 30 in lead 14 to stimulate the heart's left ventricle (LV). If the pacing mode calls for bi-ventricular pacing, the pulse generator 26 is controlled by the microprocessor-based controller 24 to deliver stimulating pulses to sites in both the right and left ventricles (BV). In accordance with contemporary techniques, the left ventricle additionally may be sequentially paced at a plurality of locations (sites).

The micro-processor-based controller 24 controls the timing of stimulating pulses at cardiac sites relative to a selected preceding depolarization signal and to each other to thereby define site-to-site pacing intervals. The system is capable of pacing in several modes and at variable site-to-site time delays in each mode. This operation may be continually upgraded by additional processed data received from the associated sensors particularly to modify the AV delay in accordance with the present invention as will be discussed. An external programmer 32 may be provided to send data signals transcutaneously to the implanted pacemaker 12 and also to receive signals originating within the pacemaker, if desired. In this fashion, a physician is capable of modifying the operating program externally or such parameters as pacing rate, pacing pulse width, pacing amplitude, sensitivity, AV delay and operations such as manually initiated data acquisition may be implemented. The external programmer may be also used to interface with an external monitor (not shown) incorporating a microprocessor and associated memory.

FIG. 2 depicts a more detailed block diagram of the microprocessor-based controller 24 shown in FIG. 1. It is conventional in its architecture and includes a microprocessor chip 34 and associated RAM and ROM memory modules 36 and 38 connected to it by an address bus 40 and a data bus 42. As is known in the art, the RAM memory 36 is a read/write memory comprising a plurality of addressable storage locations where multi-byte data, words and operands used in the execution of one or more programs may be stored for subsequent readout. The ROM memory will typically be used to store the control programs executable by the microprocessor chip 34.

Also connected to the address bus and data bus is an I/O interface module 44. If a separate analog-to-digital converter, as at 46, is utilized rather than an on-board A/D converter forming a part of the microprocessor chip 34, its output will be connected through the I/O module 44 allowing the analog outputs from the atrial sense amplifier 18 and the ventricular sense amplifier 22 and any other analog sensors involved, but not shown, to be digitized before being routed to the microprocessor chip 34. If the particular microprocessor employed incorporates an on-board A/D converter (as is somewhat more conventional), then the outputs from the A-sense amplifier 18 and the V-sense amplifier 22 and others are applied directly to appropriate inputs of the microprocessor chip 34. Also, shown coupled to the I/O module 44 is a transceiver 48 that may be used to interface the external programmer 32 to the implanted pacer 12. The manner in which an external programmer appropriately placed on the chest wall in proximity to the implanted device is capable of transmitting digitally encoded data therebetween is well known to those skilled in the pacemaker art.

Figure 5:
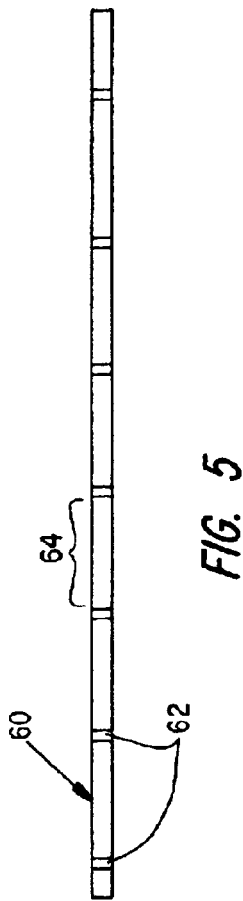
FIG. 5 is a time diagram illustrating a sequence of AVCT measurement intervals.

The optimization method of the detailed embodiment of the present invention is exemplified by the flow charts of FIGS. 7A–7C and 8. FIG. 5 depicts a timeline 60 containing a series of spaced CT measurement times indicated by stripes 62 separated by time intervals as at 64. The interval 64 preferably is set up as an odd number such as 55 minutes so that over time CT measurement times 62 occur and times representative of all patient activity levels and all times throughout all 24 hours.

In addition, the data collection system is preferably more flexible and susceptible to other triggering techniques or approaches such as manual implementation of a measurement via the external programmer 32 as when, for example, the patient undergoes a stress test or other exercise regimen beneficial to be monitored. Also, if certain portions of the activity level range lack the necessary data for template generation, arrival of the R-R, activity and/or MV in that portion can be used to trigger a data acquisition sequence event.

During each of the measurement times 62, the interval of interest, e.g., the AV interval lower rate limit or other timing parameter, is lengthened for about 8–15 beats so that intrinsic AVCT, or other CT, can be measured without interference.

Returning to FIG. 7A, using AVCT as an example, we see a programmed "start" box for an AVCT measurement sequence at 70. To allow the system to measure intrinsic AVCT while providing ventricular backup pacing, the system sets the pacing device to operate in a VDD mode with a specific lengthened AV delay, perhaps 400 msec. After a transition to this mode, the system waits through a number of cardiac cycles to determine whether normal heart operation is occurring so that valid intrinsic data may be obtained. The trending data measurement is then enabled at 72. If this is not the case and irregularities are detected, efforts are ended at 74 and no data is taken. The beginning sequence is repeated with the next programmed start signal. If conditions are such that the patient qualifies for the next step, at 76 an AVCT measurement duration interval is set which may consist of a pre-determined number of beats to be used for collecting data. At 78, the AV delay is again set to a lengthened value, perhaps, 400 msec. A train or washout period consisting of a pre-determined number of beats, perhaps involving 8 ventricular responses, is detected at 80 prior to the beats used in the gathering of usable data at 82. If the required number of intrinsic or unpaced beats is not achieved at 80, an error signal is logged at 84 and the efforts are again ended at 74. If success is achieved for intrinsic beats at 80, AVCT and other parameter data is sent for a programmed number of beats which may be, but are not necessarily, successive beats for the duration and each is also assigned to the appropriate bin at 82 as timed at 86. The data is further logged in and tagged with a date and time label at 88. Other data which may be simultaneously collected includes heart rate, cycle length, activity and minute ventilation, etc.

Figure 6:
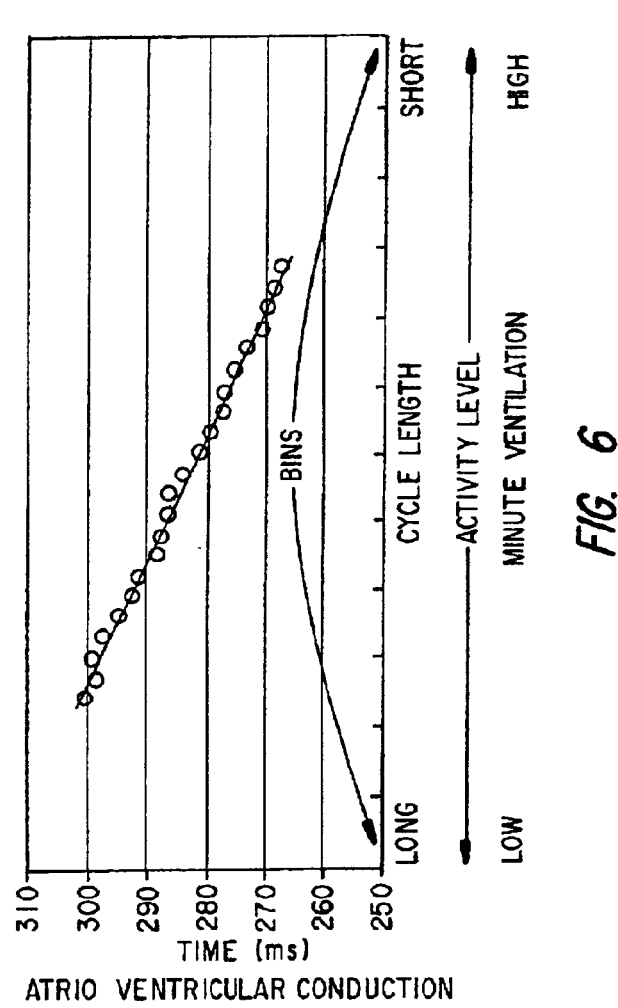
FIG. 6 is a simulated graphical template in accordance with the invention showing the relation between AVCT and several sensed parameters of interest.

As can be seen from FIG. 6, the AVCT data is accumulated in relation to data simultaneously representing another parameter of interest such as cycle length, activity level or minute ventilation. The range of these values may then be divided into a number of discrete bins as shown and the AVCT data accumulated in the appropriate bin with exponential averaging. This is part of the process included at 82 in the diagram of FIG. 7A. The exponential averaging factor can be programmable, perhaps using a default setting of 8.

Figure 7A:
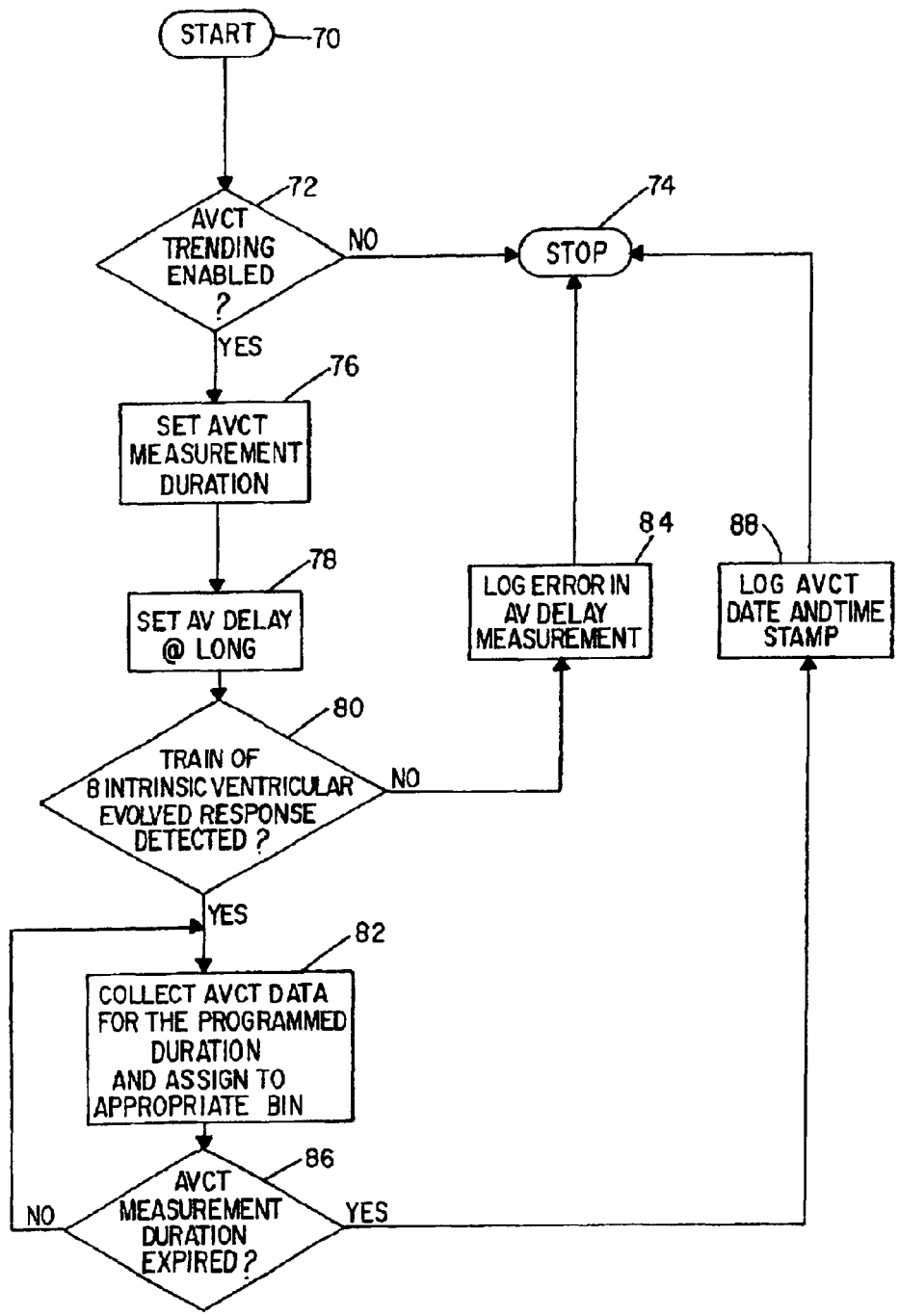
FIGS. 7A–7C are flow charts depicting the collection of AVCT data in accordance with the invention.
Figure 7B:
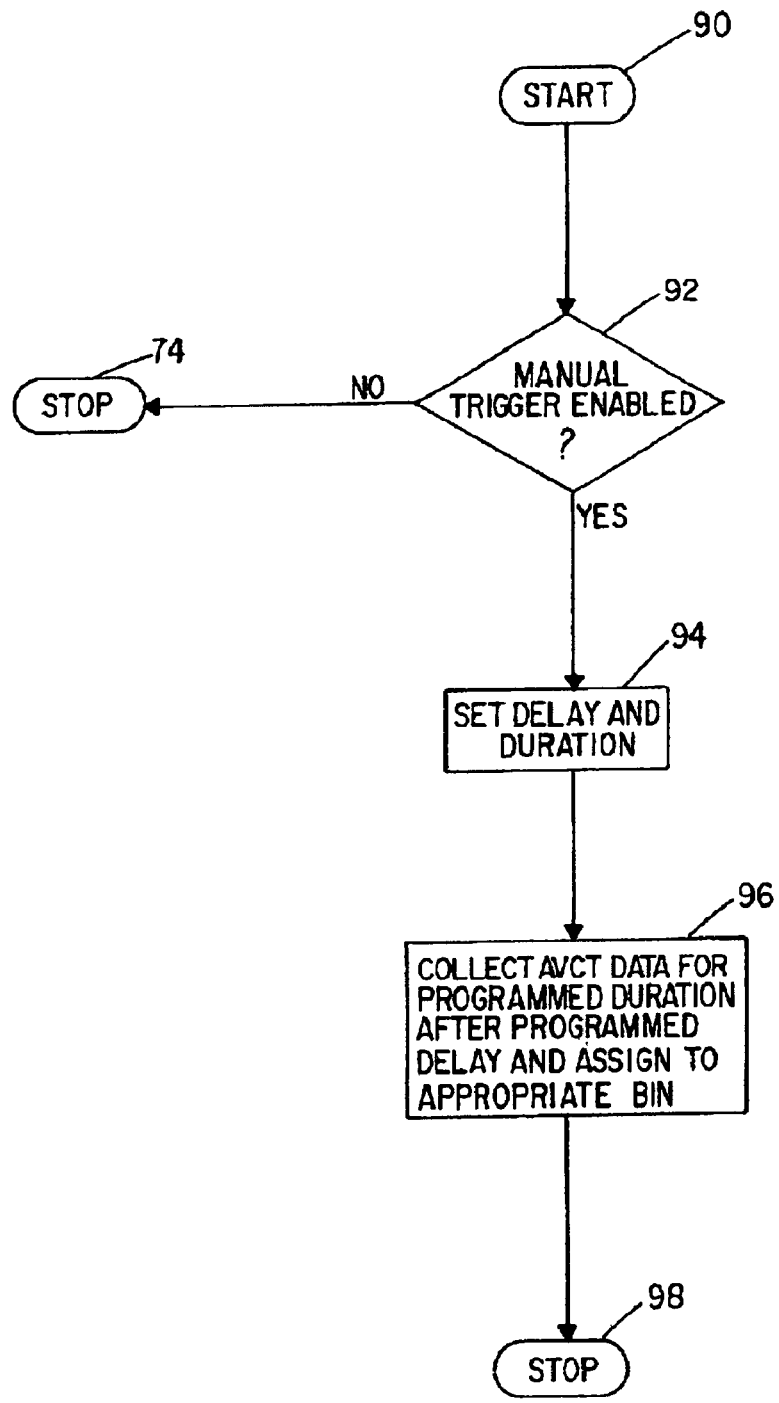

An alternative manually implemented AVCT data collection routine is also shown at FIG. 7B, which starts at 90 upon the receipt of an external signal. As was the case with the programmed data acquisition implementation, the manual data sequence must be enabled at 92 and if this does not occur, the attempt is again ended at 74. If it is determined that the manual trigger is enabled at 92, a delay or washout period is set as is the duration of the data acquisition period in block 94. This having been done, AVCT data is collected for the programmed duration, processed and assigned to the bins at 96 as was the case at 82 after the expiration of the washout or delay period at 94. After the data has been acquired for the programmed duration and assigned as appropriate, the manual data collection routine is ended at 98.

Figure 7C:
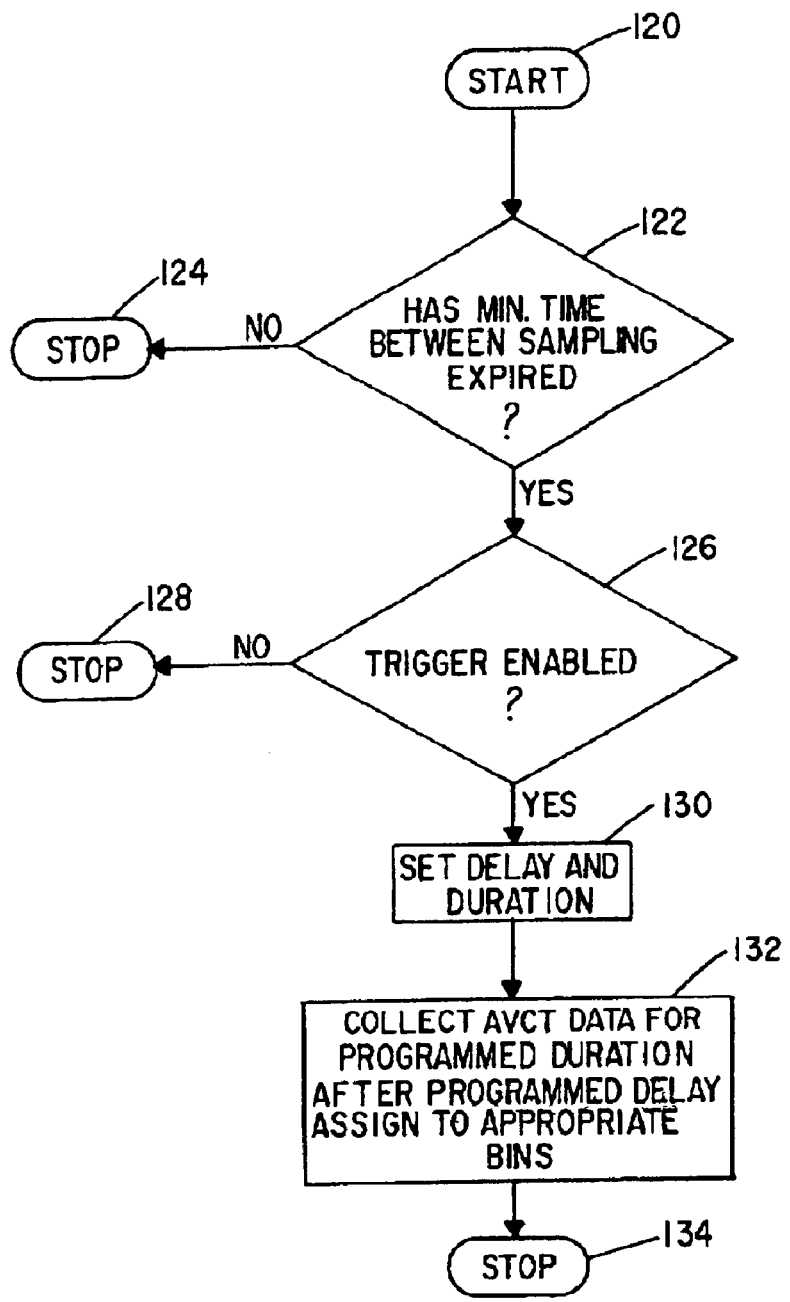

FIG. 7C depicts yet another data acquisition flow chart biased for the acquisition of data to help fill bins which, after a period of time, still show a data shortfall. Here a routine may be triggered when the system senses that one of the associated parameters has fallen into a range for which corresponding AVCT or other conduction time data is then presently insufficient with respect to proper template generation or updating. The criteria for such an event to occur is, of course, preprogrammed into the system where desired and may be based on, for example, the monitored heart rate falling into a range of scarce corresponding data. When this occurs, a AVCT or other data collection routine would be started at 120. An additional enabling factor is interposed at 122 to require a minimum time between sampling or data acquisition events which may be, for example, 20 minutes. If this has not occurred, the collection routine will be stopped at 124. If the answer at 122 is "yes", as was the case with the program and manually triggered data acquisition implementations, the data sequence must also be enabled in the manner of routines 7A and 7B at 126. If this does not occur, the attempt is again ended at 128. If it is determined that the trigger is enabled at 126, a delay or washout period is set as is the duration of the data acquisition period in block 130. This having been accomplished, AVCT data is collected for the programmed duration as shown at 132 and assigned to the bins as was the case at 82 in FIG. 7A. In the manner of the other collection routines, after the data has been acquired for the program duration and assigned as appropriate, the data collection is ended at 134.

Figure 8:
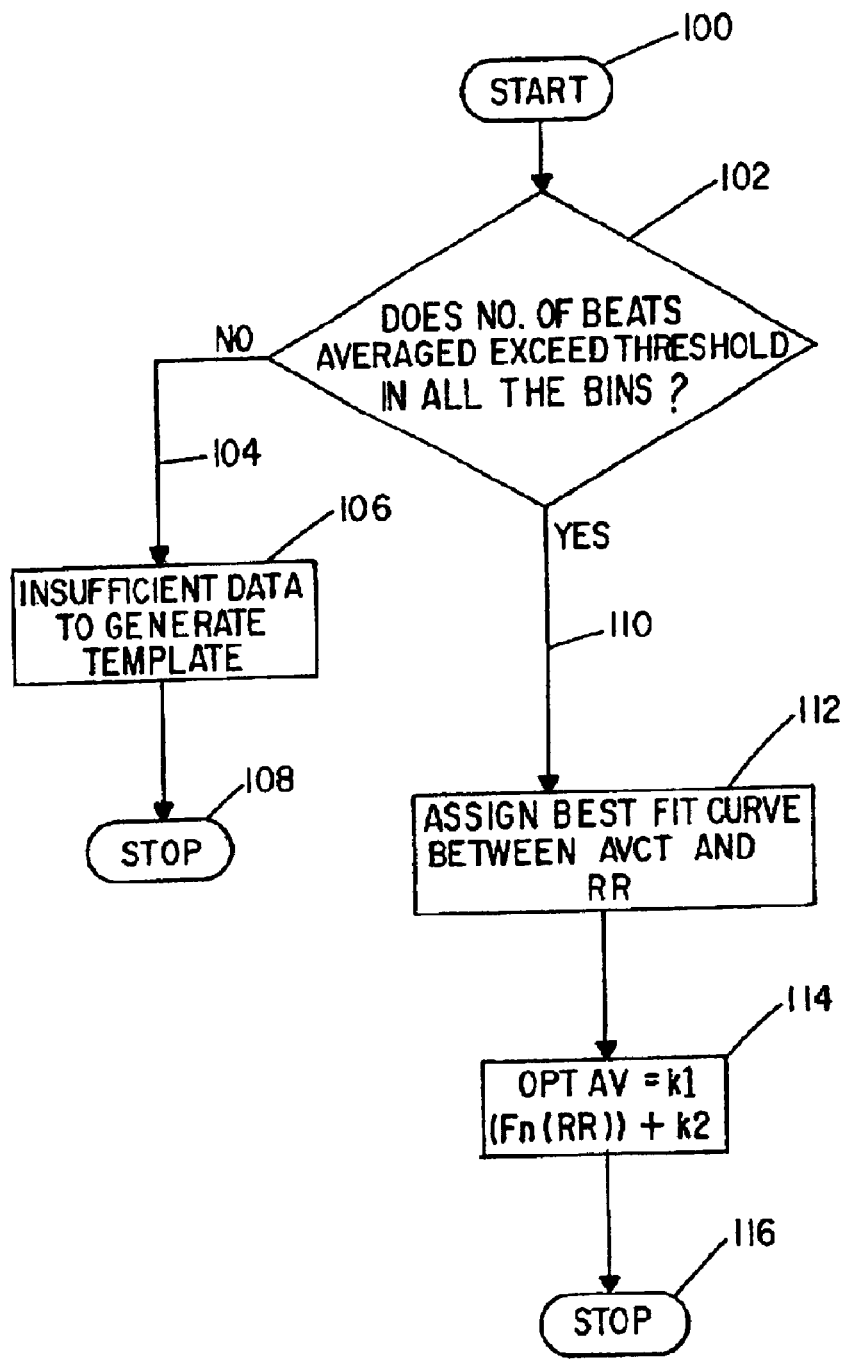
FIG. 8 is a flow diagram depicting the generation of an optimum AV delay from the data gathered in FIGS. 7A–7C.

FIG. 8 depicts one possible flow chart associated with the generation of a template such as that shown in FIG. 6 in accordance with the present invention. As previously indicated, before template generation can be initiated, there must be sufficient data assigned to a sufficient number of bins in the given AVCT time versus chosen parameter (cycle length, activity level, minute ventilation, etc.) to produce what has been pre-programmed or established as a minimum valid template. In accordance with the template generation of FIG. 8, template generation or updating may start after the taking of data in accordance with the flow charts of FIGS. 7A–7C at 100. As seen in decision block 102, this protocol requires sufficient data to be averaged into all of the bins prior to template generation. If this is not the case when the data is tested, a signal exists at 104 and is registered as indicative of insufficient data to generate a template at 106 and the attempt at template generation is stopped at 108.

Conversely, if sufficient data does exist, the signal exits at 110 and a best-fit curve is designed between AVCT and, in this case as an example, cycle length R-R at 112. The best-fit curve may be constructed based on a mathematical best-fit (linear, quadratic or higher order polynomial) between AVCT and R-R (activity or MV levels or other designated parameter of interest). The relationship between ACVT and R-R can also be described by means of a lookup table. An alternative protocol may be provided which tolerates fewer beats or missing data in one or more of the bins and which utilizes interpolation or extrapolation through the missing bins as required.

A mathematical operator is applied as a function of the cycle length or other chosen parameter of interest at 114. This may be done in accordance with the mathematical relationship developed in the above-mentioned Jiang Ding et al U.S. Pat. No. 6,144,880. This may be generally described by optimum AV delay=$K_1$(fn(R-R or activity level or MV level))+$K_2$ wherein $K_1$ is a generally empirically determined non-zero constant and $K_2$ is the offset constant that can be positive, negative or zero and fn is a determined function. The program exits at 116.

An important aspect of the present invention lies in the fact that after a template is generated and an optimum AV delay determined from that, data acquisition does not end, but is continually accumulated and periodically newer updated templates are generated when the new data meets the criteria for the generation of an updated template.

The optimized AV delay function can be used to suggest to the user either a fixed or dynamic AV delay value. For example, if the patient's heart rate is concentrated around a particular value, a fixed AV delay can be set based on that particular rate and this fixed AV delay updated and the template is updated with new data. If, however, the patient's activity is such that the patient's heart rate varies over a larger range, dynamic AV delay may be suggested which changes according to the patient's level of activity. Although the best-fit curve shown in FIG. 6 is simulated as a linear fit, as indicated, any higher order rotation can be constructed as necessary for a best fit to the data.

We have described the aspects of the present invention with particular reference to measuring AVCT and, in turn, generating from that an updatable template which can be used to establish either a fixed or dynamic AV delay value. Beyond this embodiment, however, the invention suggests broader aspects and applications manifested in other embodiments.

Figure 9:
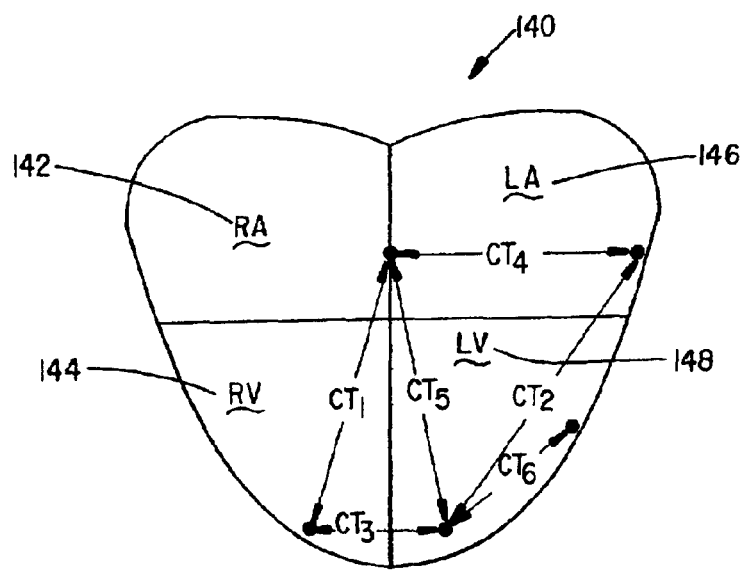
FIG. 9 is a schematic representation of a heart showing plurality of conduction times that can be measured and trended with respect to sensed parameters of interest.

In this regard, FIG. 9 depicts a schematic diagram of a heart 140 divided into the four chambers and further illustrating schematically a variety of conduction times ($CT_1$–$CT_6$) for which data can be acquired and based upon which pacing delays may be correspondingly determined or adjusted. In this manner, the conduction time between the right atrium 142 and right ventricle 144 (RA-RV) is shown as $CT_1$ and may, where appropriate, be related to the pacing delay between those chambers. Likewise, the conduction time and pacing delay between the left atrium 146 and left ventricle 148 (LA-LV) is illustrated by the line $CT_2$; $CT_3$ is between the right ventricle, RV, and the left ventricle LV, (V-V) $CT_4$ is between RA and LA (if the LA requires pacing); $CT_5$ lies between RA and LV; and $CT_6$ represents the conduction time and possible optimization of the pacing delay between $LV_1$ and $LV_2$ with respect to dual pacing sites in the left ventricle.

Figure 10:
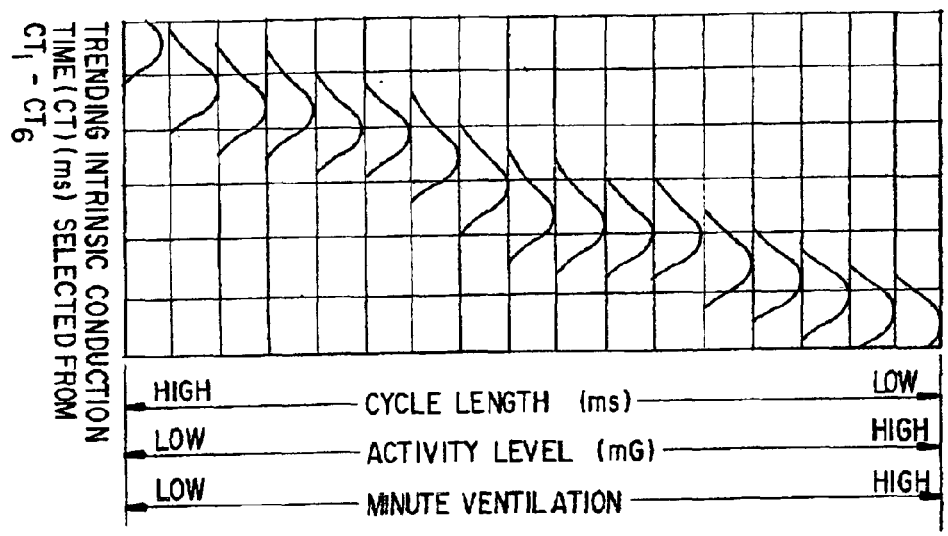
FIG. 10 is a simulated graphical template in accordance with the invention showing the relation between any of several sensed conduction times and R-R, activity level or MV level.

In this manner, the gathering of data between other pairs of points or even multiple pairs during simultaneous beats may enable resynchronization therapy in accordance with the invention to be applied throughout the heart. Data may be acquired from all CT's, i.e., 1–6 can be measured during the same data acquisition enablements and trended with respect to R-R, activity level or MV level. An illustration of this appears graphically in FIG. 10, which depicts a relationship which could be for any of the CT's involved. The value in each bin can be exponentially averaged as each new value enters.

It will also be appreciated that, as the data acquisition proceeds, the accumulated charting data, for example, can also be made available to the diagnosing or treating physician for review. In this manner collected data can be used to characterize the patient's status and to show worsening and/or improving condition with respect to the paced heart.

In addition, while the illustrated embodiments have disclosed a system for accumulating data in a series of discrete bins in relation to one or more parameters of interest, other data evaluation systems may be utilized in attempting to fit the data in relation to the parameter of interest. For example, each data point stored in memory may be stored as a bit of data or scatter point rather than being put in a discrete bin.

A sufficient collection of scatter points within the range of the parameter of interest may subsequently be utilized to generate the template and, based on a best fit curve, be modified by each new data point obtained. This also allows determination as to whether certain conduction times or delays are actually related by some function to the parameters of interest such as R-R, activity level and MV in a usable manner, for instance, by calculating a magnitude of correlation.

This invention has been described herein in considerable detail in order to comply with the Patent Statutes and to provide those skilled in the art with the information needed to apply the novel principles and to construct and use embodiments of the example as required. However, it is to be understood that the invention can be carried out by specifically different devices and that various modifications can be accomplished without departing from the scope of the invention itself.

What is claimed is:

1. A method of optimizing atrio-ventricular delay over a patient's full range of activity for use in operating an implantable cardiac pacing device comprising the steps of:
   (a) measuring atrio-ventricular conduction time for a plurality of beats and logging the values based on periodic repeating programmable sampling intervals to produce cumulative data;
   (b) constructing a current template of atrio-ventricular conduction time in relation to one or more other sensed parameters of interest over said full range of patient activity levels from the said cumulative data;
   (c) based on a then current template derive a suggested optimum atrio-ventricular delay; and
   (d) wherein the data from each measurement is based on a discrete number of beats and is processed by exponential averaging and stored in incremental bins according to the value of the related parameter of interest and wherein a minimum number of beats must be averaged in a minimum number of bins to trigger template generation including updating.

2. A method as in claim 1 wherein the parameter of interest is selected from cycle length, activity level and minute ventilation.

3. A method as in claim 2 wherein the template is generated based on a best fit mathematical relation between atrio-ventricular conduction time and the parameter of interest.

4. A method as in claim 2 wherein said suggested optimum atrio-ventricular delay is a dynamic atrio-ventricular delay that changes as a function of one or more of said sensed parameters of interest.

5. A method as in claim 1 wherein the template is generated based on a best fit mathematical relation between atrio-ventricular conduction time and the parameter of interest.

6. A method as in claim 1 wherein the template is generated based on a programmed look-up table.

7. A method as in claim 1 wherein the programmable sampling intervals are such that sampling occurs at different times in successive 24-hour periods, such that eventually sampling occurs throughout said 24-hour period.

8. A method as in claim 1 further including a step of enabling a manual trigger mode that will force trending of atrio-ventricular conduction time during a specific intervention.

9. A method as in claim 8 wherein said intervention is a specific exercise test.

10. A method as in claim 8 wherein the measurement of said atrio-ventricular conduction time includes lengthening the then current AV delay so that intrinsic measurements can be made.

11. A method as in claim 1 wherein the collection of atrio-ventricular conduction time data is triggered based on a sensed parameter value.

12. A method as in claim 11 wherein the measurement of said atrio-ventricular conduction time includes lengthening the then current AV delay so that intrinsic measurements can be made.

13. A method as in claim 1 wherein the atrio-ventricular conduction time is measured based on a selected morphological marker of ventricular depolarization and the atrio-ventricular delay is increased above the intrinsic atrio-ventricular delay during such measurements.

14. An implantable cardiac rhythm management device programmed to operate in accordance with claim 1.

15. A method as in claim 1 wherein said cardiac conduction time is selected from (RA-RV), (LA-LV) and RA-LV).

16. A method as in claim 1 further comprising the step of programming the suggested optimum atrio-ventricular delay into the operation of said pacing device.

17. A method as in claim 1 further including the step of periodically updating said template with new atrio-ventricular conduction time data to construct a new current template.

18. A method as in claim 17 further comprising the step of changing the atrio-ventricular delay automatically when the template is updated with a new atrio-ventricular conduction time delay.

19. A method as in claim 18 wherein said suggested optimum atrio-ventricular delay is a fixed atrio-ventricular delay.

20. A method as in claim 1 wherein said suggested optimum atrio-ventricular delay is a dynamic atrio-ventricular delay that changes as a function of one or more of said sensed parameters of interest.

21. A method as in claim 1 wherein said suggested optimum atrio-ventricular delay is a fixed atrio-ventricular delay.

22. A method as in claim 1 wherein the measurement of said atrio-ventricular conduction time includes lengthening the then current AV delay so that intrinsic measurements can be made.

23. A method as in claim 1 wherein said periodic repeating programmable sampling intervals require a minimum time between data acquisition.

24. A method as in claim 1 wherein data acquisition must be enabled in the manner of a predetermined routine.

* * * * *